(12) United States Patent
Wang

(10) Patent No.: US 7,696,222 B2
(45) Date of Patent: Apr. 13, 2010

(54) INDOLE DERIVATIVES AS CRTH2 RECEPTOR ANTAGONISTS

(75) Inventor: Zhaoyin Wang, Kirkland (CA)

(73) Assignee: Merck Frosst Canada Ltd, Quebec (CA)

(*) Notice: Subject to any disclaimer, the term of this patent is extended or adjusted under 35 U.S.C. 154(b) by 235 days.

(21) Appl. No.: 11/990,378

(22) PCT Filed: Aug. 7, 2006

(86) PCT No.: PCT/CA2006/001305

§ 371 (c)(1),
(2), (4) Date: Feb. 11, 2008

(87) PCT Pub. No.: WO2007/019675

PCT Pub. Date: Feb. 22, 2007

(65) Prior Publication Data

US 2009/0286825 A1    Nov. 19, 2009

Related U.S. Application Data

(60) Provisional application No. 60/708,043, filed on Aug. 12, 2005.

(51) Int. Cl.
*A01N 43/42* (2006.01)
*A61K 31/44* (2006.01)
*A61K 31/40* (2006.01)
*A01N 43/38* (2006.01)
*C07D 451/00* (2006.01)
*C07D 453/00* (2006.01)
*C07D 455/00* (2006.01)
*C07D 487/00* (2006.01)

(52) U.S. Cl. .................. 514/294; 514/411; 546/94; 548/428

(58) Field of Classification Search .................. 514/294, 514/411; 546/94; 548/428
See application file for complete search history.

(56) References Cited

U.S. PATENT DOCUMENTS

| 4,965,258 | A | 10/1990 | Boshagen et al. |
| 7,144,913 | B2 | 12/2006 | Wang et al. |

FOREIGN PATENT DOCUMENTS

| EP | 1 505 061 | 5/2003 |
| WO | WO 2005/040114 | 5/2005 |

OTHER PUBLICATIONS

Lee et al., Journal of Organic Chemistry (1999), 64(12), 4224-4225.*
Shichijo, et al., "Chemoattractant Receptor-Homologous Molecule Expressed on TH2 Cells Activation in Vivo Increases Blood . . . ", Journal of Pharmacology (2003), vol. 307, No. 2, p. 518-525.
Chevalier, et al., "Cutting Edge: Chemoattractant Receptor-Homologous Molecule Expressed on TH2 Cells Plays a Restricting Role on IL-5 . . . ", Journal of Immunology (2005), vol. 175, No. 4, pp. 2056-2060.
Ulven, et al., "Minor Structural Modifications Convert the Dual TP/CRTH2 Antagonist Ramatroban into a Highly Selective . . . ", Journal of Medicinal Chemistry (Feb. 24, 2005), vol. 48, No. 4, pp. 897-900.

* cited by examiner

*Primary Examiner*—D. Margaret Seaman
*Assistant Examiner*—Niloofar Rahmani
(74) *Attorney, Agent, or Firm*—Mollie M. Yang; Valerie J. Camara

(57) ABSTRACT

Compounds according to formula (I) wherein the radicals $R^1$, $R^2$ and $R^3$ are as herein defined, and wherein Ar represents an aryl group or heteroaryl group, preferably phenyl, n is 1 or 2, and the radical X represents a group selected from —C($R^a$)($R^b$)—, —C($R^a$)($R^b$)—C($R^a$)($R^b$)—, —C($R^a$)=C($R^a$)—, OC($R^a$)($R^b$)— or SC($R^a$)($R^b$)—. These compounds and their pharmaceutical acceptable salts are used in pharmaceutical compositions as prostaglandine D2 receptor antagonists useful in the treatment of CRTH2-mediated diseases such as respiratory, inflammatory or allergic conditions among others.

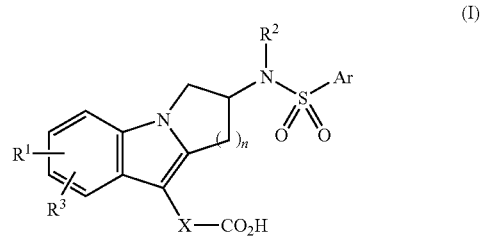

(I)

10 Claims, No Drawings

INDOLE DERIVATIVES AS CRTH2 RECEPTOR ANTAGONISTS

CROSS REFERENCE TO RELATED APPLICATIONS

This application is a U.S. National Phase application under 35 U.S.C. § 371 of PCT Application No. PCT/CA2006/001305, filed Aug. 7, 2006, which claims priority under 35 U.S.C. § 119(e) from U.S. Provisional Application Ser. No. 60/708,043, filed Aug. 12, 2005.

BACKGROUND OF THE INVENTION

Prostanglandin $D_2$ ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

Ulven and Kostenis, *J. Med. Chem.*, 2005, 48(4):897-900 reports the synthesis of analogs of ramatroban that are selective potent CRTH2 antagonists. CRTH2 antagonists are also reported in PCT Published Application WO2003/097598.

SUMMARY OF THE INVENTION

The present invention provides novel compounds which are CRTH2 receptor antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

and pharmaceutically acceptable salts thereof, wherein:
n is 1 or 2;
Ar is aryl or heteroaryl each optionally substituted with 1 to 4 groups independently selected from $R^c$;
X is selected from —$C(R^a)(R^b)$—, —$C(R^a)(R^b)$—$C(R^a)(R^b)$—, —$C(R^a)$=$C(R^a)$—, —$OC(R^a)(R^b)$—, and —$SC(R^a)(R^b)$—;
$R^1$ is selected from H, halogen and $C_{1-6}$alkyl;
$R^2$ is selected from H and $C_{1-6}$alkyl;
$R^3$ is selected from H, halogen, $C_{1-6}$alkyl, $OC_{1-6}$alkyl, $SC_{1-6}$alkyl, $S(O)_nC_{1-6}$alkyl, CN, aryl and heteroaryl;
$R^a$ and $R^b$ are independently H, halogen, aryl, heteroaryl, $C_{1-6}$alkyl or halo$C_{1-6}$alkyl; or
$R^a$ and $R^b$ together with the carbon atom to which they are both attached complete a $C_{3-6}$cycloalkyl ring; or
$R^a$ and $R^b$ together with the adjacent carbon atoms to which they are attached complete a $C_{3-6}$cycloalkyl ring; and
$R^c$ is selected from halogen, CN, $C_{1-6}$alkoxy, $C_{1-6}$alkyl, halo$C_{1-6}$alkoxy, and halo$C_{1-6}$alkyl.

In one subset of formula I are compounds wherein n is 1; and in another subset are compounds wherein n is 2.

In another subset of formula I are compounds wherein Ar is phenyl optionally substituted with 1 to 3 groups independently selected from $R^c$. In one embodiment thereof Ar is phenyl substituted with 1 to 2 groups independently selected from halogen and $C_{1-6}$alkoxy.

In another subset of formula I are compounds wherein X is —$C(R^a)(R^b)$—. In one embodiment thereof X is methylene.

In another subset of formula I are compounds wherein X is —$C(R^a)(R^b)$—$C(R^a)(R^b)$—, or —$C(R^a)$=$C(R^a)$—. In one embodiment thereof X is —CH=CH— or —$CH_2CH_2$—

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear or branched alkyl chains containing the indicated number of carbon atoms. Non-limiting examples of alkyl groups include methyl, ethyl, propyl, isopropyl, butyl, s- and t-butyl, pentyl, hexyl, heptyl, and the like.

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes —$CF_3$, —$CF_2CF_3$ and the like.

"Alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. $C_{1-6}$haloalkoxy, for example, includes —$OCF_3$, —$OCF_2CF_3$ and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl.

The term "heteroaryl" (Het) as used herein represents a 5-10 membered aromatic ring system containing one ring or two fused rings, 1-4 heteroatoms, selected from O, S and N. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "prophylaxis" means preventing or delaying the onset or the progression of a disease or disorder, or the signs and symptoms associated with such disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

For purposes of this specification, the following abbreviations have the indicated meanings Ac=acetyl; AcO=acetate; BOC=t-butyloxycarbonyl; CBZ=carbobenzoxy; CDI=carbonyldiimidazole; DCC=1,3-dicyclohexylcarbodiimide; DCE=1,2-dichloroethane; DIBAL=diisobutyl aluminum hydride; DIEA=N,N-diisoproylethylamine; DMAP=4-(dimethylamino)pyridine; DMF=dimethylformamide; EDCI=1-(3-dimethylaminopropyl)-3-ethylcarbodiimide HCl; EDTA=ethylenediaminetetraacetic acid, tetrasodium salt hydrate; FAB=fast atom bombardment; FMOC=9-fluorenylmethoxycarbonyl; HMPA=hexamethylphosphoramide; HATU=O-(7-azabenzotriazol-1-yl)-N,N,N',N'-tetramethyluronium hexafluorophosphate; HOBt=1-hydroxybenzotriazole; HRMS=high resolution mass spectrometry; ICBF=isobutyl chloroformate; KHMDS=potassium hexamethyl-disilazane; LDA=lithium diisopropylamide; MCPBA=metachloroperbenzoic acid; MMPP=magnesium monoperoxyphthlate hexahydrate; Ms=methanesulfonyl=mesyl; MsO=methanefulfonate=mesylate; NBS=N-bromosuccinimide; NMM=4-methylmorpholine; PCC=pyridinium chloro-chromate; PDC=pyridinium dichromate; Ph=phenyl; PPTS=pyridinium p-toluene sulfonate; pTSA=p-toluene sulfonic acid; PyH.Br$_3$=pyridine hydrobromide perbromide; r.t.=room temperature; rac.=racemic; TFA=trifluoroacetic acid; TfO=trifluoromethanesulfonate=triflate; THF=tetrahydrofuran; TLC=thin layer chromatography. Alkyl group abbreviations include: Me=methyl; Et=ethyl; n-Pr=normal propyl; i-Pr=isopropyl; c-Pr=cyclopropyl; n-Bu=normal butyl; i-Bu=isobutyl; c-Bu=cyclobutyl; s-Bu=secondary butyl; t-Bu=tertiary butyl.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethyl-piperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I are meant to also include the pharmaceutically acceptable salts.

Utilities

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer.

Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compounds of formula I are antagonists of prostaglandin D2 receptor, CRTH2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a DP receptor antagonist such as S-5751; (2) a corticosteroid such as triamcinolone acetonide; (3) a β-agonist such as salmeterol, formoterol, terbutaline, metaproterenol, albuterol and the like; (4) a leukotriene modifier, including a leukotriene receptor antagonist or a lipooxygenase inhibitor such as montelukast, zafirlukast, pranlukast, or zileuton; (5) an antihistamine such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxy-loratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin $D_2$ mediated diseases comprising: administration to a patient in need of such treatment a non-toxic therapeutically effective amount of a compound of formula I, optionally co-administered with one or more of such ingredients as listed immediately above.

Methods of Synthesis

Compounds of Formula I of the present invention can be prepared according to the synthetic routes outlined in Schemes 1 to 8 and by following the methods described herein.

Method 1

Reduction of ethyl indole-2-carboxylate 1 followed by oxidation gives aldehyde 2. Wittig reaction of 2 with a phosphorane provides α,β-unsaturated ester 3, which is alkylated with t-butyl bromoacetate and a base to give diester 4. Hydrogenation of 4 followed by base-promoted cyclization yields the cyclic β-ketoester 5. Decarboxylation of 5 with silica gel in refluxing toluene gives ketone 6. Reduction of 6 with $NaBH_4$ affords alcohol 7, which can be converted to azide 8 by mesylation followed by displacement with sodium azide. Reduction of 8 under hydrogenation conditions provides the corresponding amine, and the amine intermediate can react with a variety of arylsulfonyl chlorides, followed by optionally alkylation, to give aryl sulfonamide 9. Reaction of 9 with oxalyl chloride, followed by esterification with MeOH, yields α-keto ester 10. Deoxygenation of 10 can be achieved by reduction with $NaBH_4$ followed by $Et_3SiH$ in TFA to provide ester 11. Hydrolysis of 11 in aqueous base yields the final product 12.

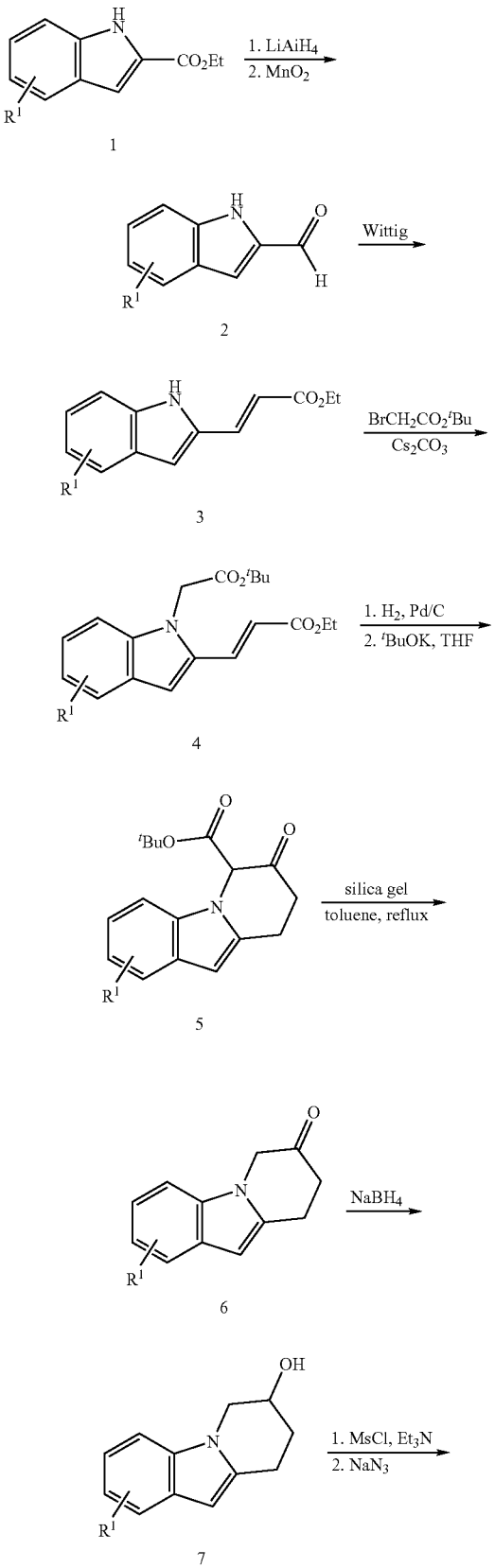

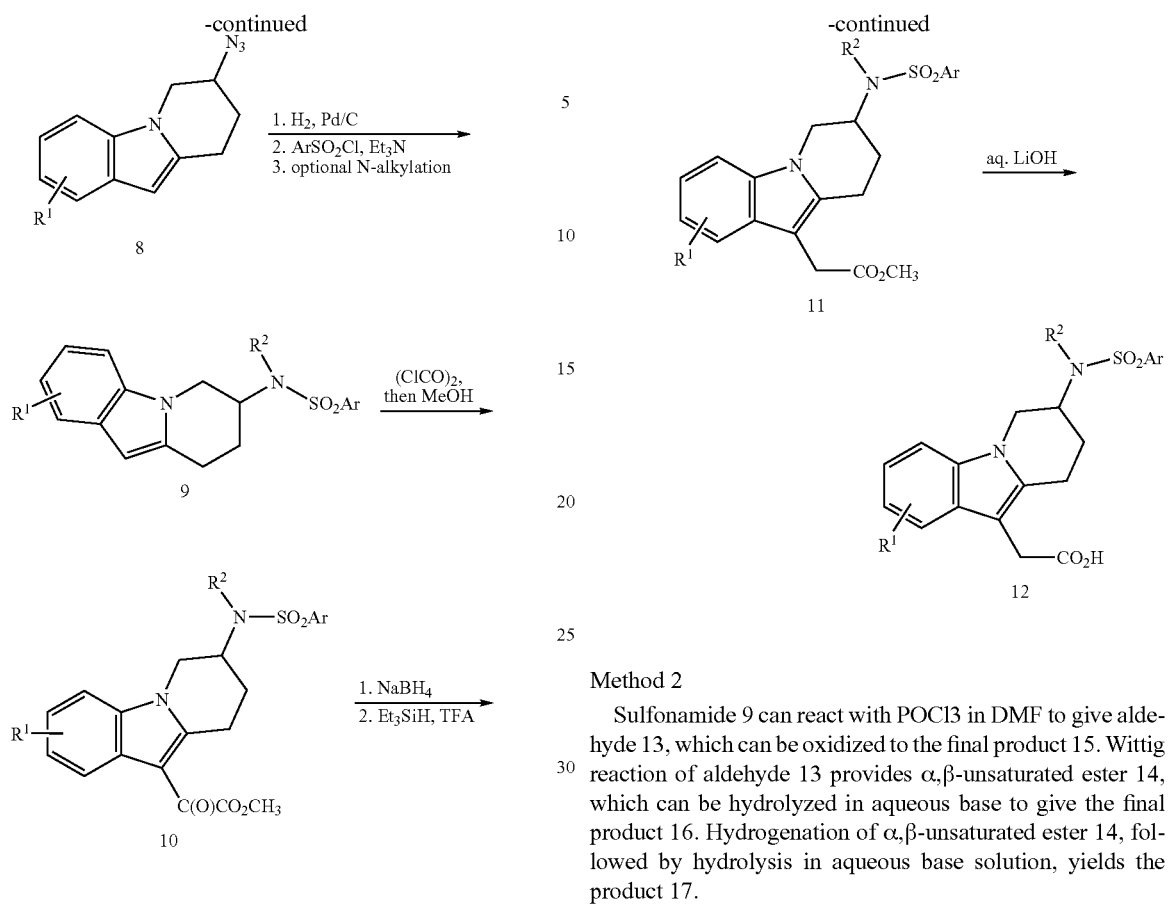
Method 2
Sulfonamide 9 can react with POCl3 in DMF to give aldehyde 13, which can be oxidized to the final product 15. Wittig reaction of aldehyde 13 provides α,β-unsaturated ester 14, which can be hydrolyzed in aqueous base to give the final product 16. Hydrogenation of α,β-unsaturated ester 14, followed by hydrolysis in aqueous base solution, yields the product 17.
SCHEME 2
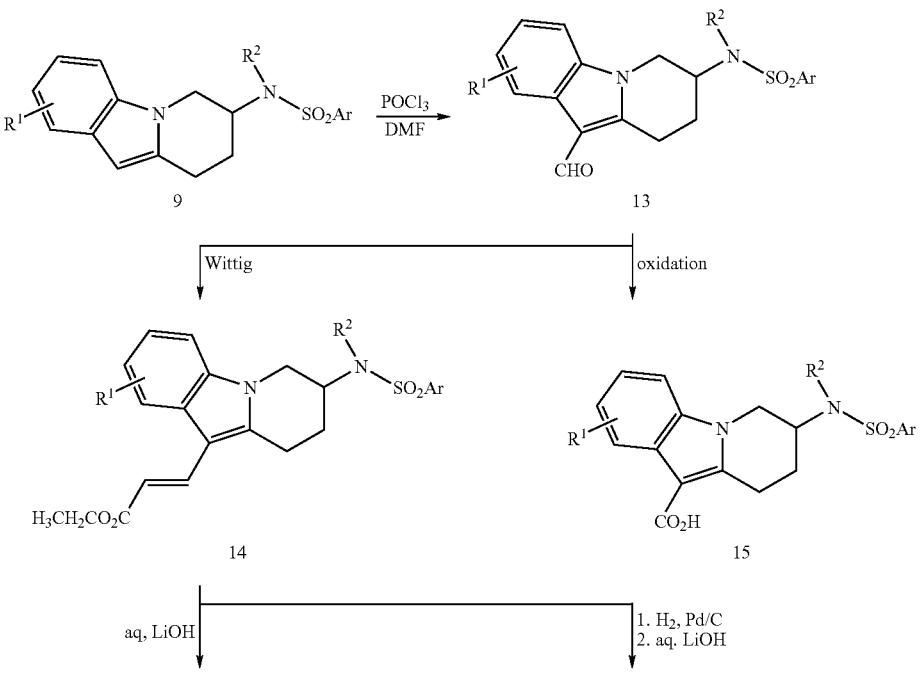

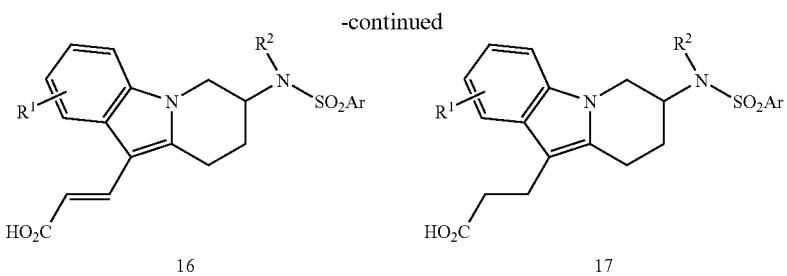

Method 3

Sulfonamide 9 can react with (SCH$_2$CO$_2$Me)$_2$ and sulfuryl chloride in dichloroethane to give sulfide 18, which can be hydrolyzed to the final product 19 in aqueous base solution.

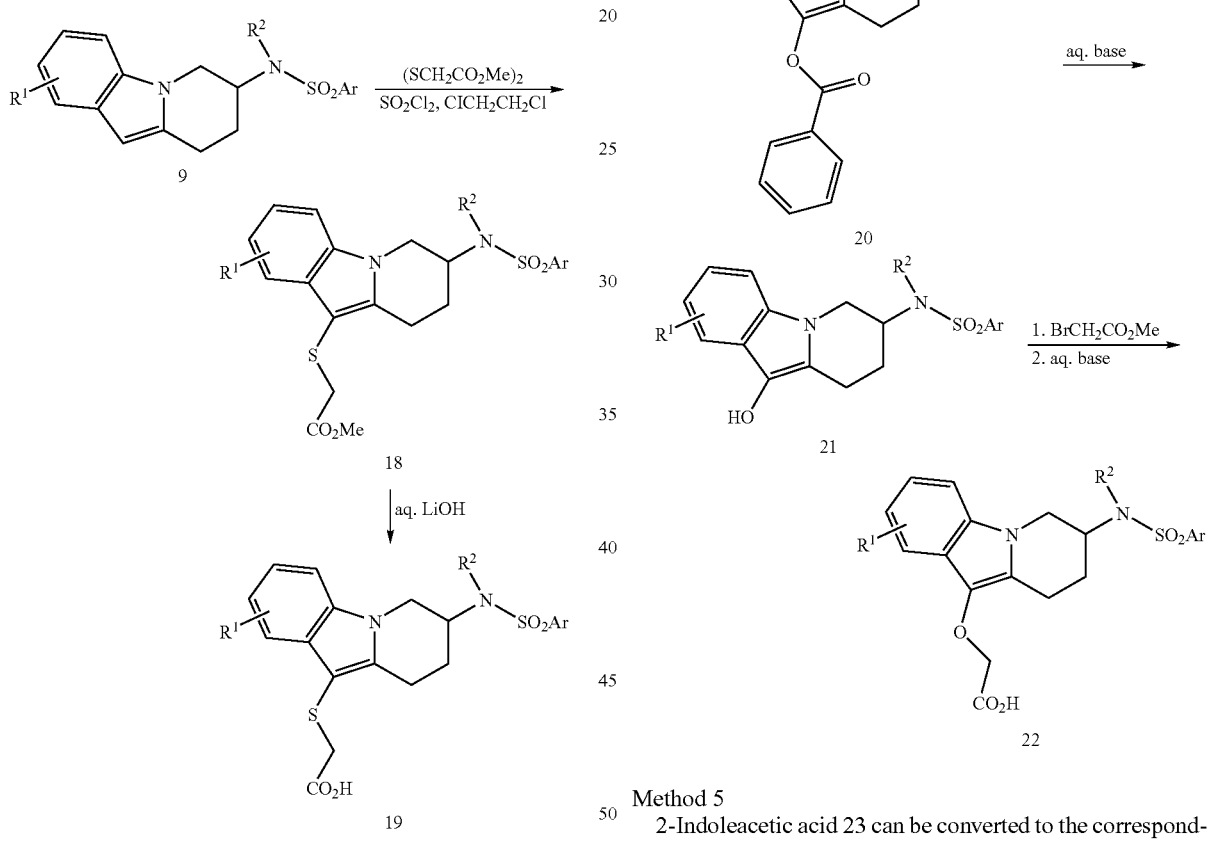

Method 4

Sulfonamide 9 can react with benzoyperoxide to give benzoate 20. Hydrolysis of 20, followed by alkylation with bromoacetate, can provide ester 21, which can be hydrolyzed to the final product 22 in aqueous base solution.

Method 5

2-Indoleacetic acid 23 can be converted to the corresponding t-Butyl ester 24. Alkylation of 24 with methyl bromoacetate and a base provides diester 25. Base-promoted cyclization of 25 yields the cyclic β-ketoester 26. Decarboxylation of 26 with silica gel in refluxing toluene gives ketone 27. The desired product 28 can be prepared by following the steps described in Method 1.

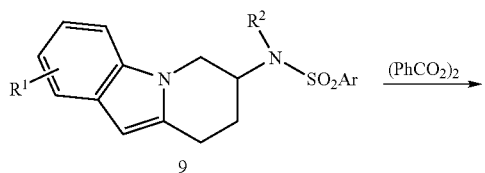

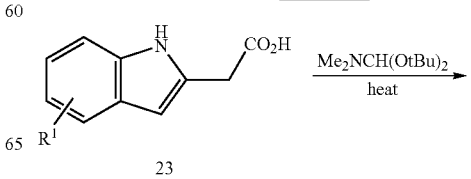

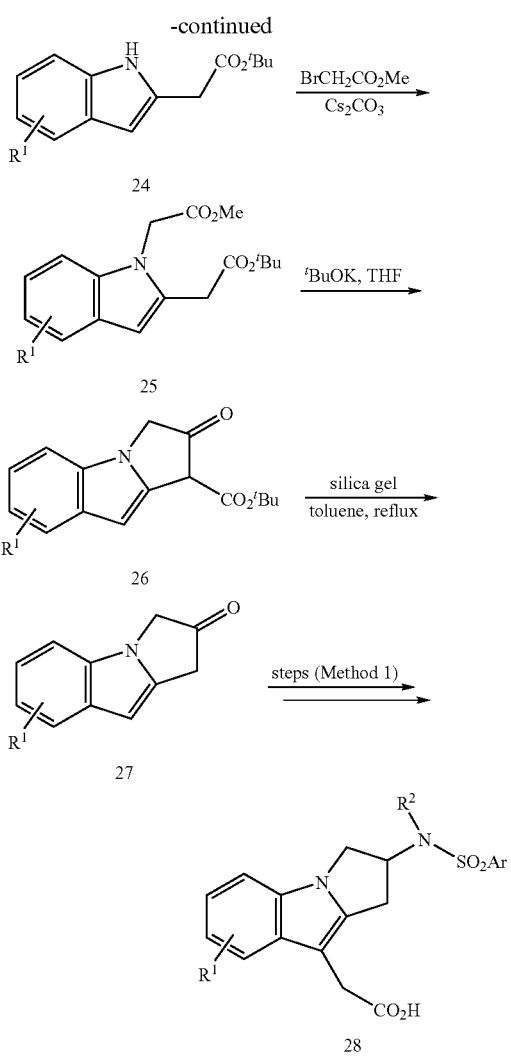

The following examples are provided to illustrate the invention and are not to be construed as limiting the scope thereof in any manner.

Example 1

(+/−){7-[[(4-Fluorophenyl)sulfonyl](methyl)amino]-6,7,8,9-tetrahydropyrido[1,2-a]indol-10-yl}acetic acid

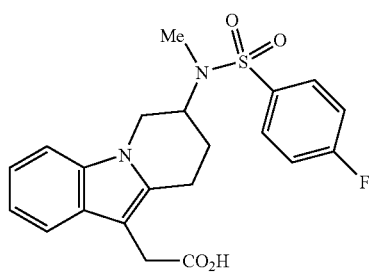

Step 1: 1H-indole-2-carbaldehyde

To a solution of ethyl indole-2-carboxylate (20 g) in 200 mL of THF cooled at −78° C. was added 110 mL of 1 M solution LiAlH$_4$ in THF. The reaction mixture was stirred between −78° C. and 0° C. for 1 h, and then quenched by slow addition of 125 mL of 4N HCl followed by 150 mL of water. The reaction mixture was extracted with 1 L of 1:1 EtOAc/hexane and the extract was dried over Na$_2$SO$_4$. Filtration and concentration provided the crude alcohol, which was dissolved in 1.2 L of CH$_2$Cl$_2$ and treated with 100 g of MnO$_2$. After stirring for 2 h, the mixture was filtered through celite and the filtrate was used for the next step without further purification.

Step 2: ethyl (2E)-3-(1H-indol-2-yl)acrylate

To the CH$_2$Cl$_2$ solution of the product of Step 1 was added 36 g of Ph$_3$P=CHCO$_2$Et. After stirring for 12 h, the reaction mixture was concentrated and the residue was purified by silica gel chromatography eluted with 1:1 EtOAc/hexane to give 20 g of the title compound as a yellow solid.

Step 3: ethyl (2E)-3-[1-(2-tert-butoxy-2-oxoethyl)-1H-indol-2-yl]acrylate

To a solution of the product of Step 2 (20 g) in 300 mL of DMF was added 30 g of BrCH$_2$CO$_2$-t-Bu and 65 g of Cs$_2$CO$_3$. The reaction mixture was stirred at 60° C. for 24 h, and was then diluted with 300 ml of acetone and filtered. The filtrate was concentrated and the residue was purified by silica gel chromatography eluted with 1:2 EtOAc/hexane to give 30 g of the title compound as a syrup.

Step 4: tert-butyl 7-oxo-6,7,8,9-tetrahydropyrido[1,2-a]indole-6-carboxylate

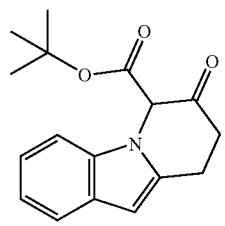

A solution of the product from Step 3 (30 g) and Pd/C (10%, 2 g) in 300 mL EtOAc was stirred under a balloon pressure of hydrogen for 12 h. The reaction mixture was then filtered through celite and the filtrate was concentrated to give the diester intermediate. The crude diester (26 g) was dissolved in 200 mL of THF and added through a dropping funnel to a chilled (−10° C.) solution of t-BuOK (82 mL, 1 M in THF) in 1 L of THF. The reaction mixture was warmed to room temperature over a period of 10 min and treated with 100 ml of 1 N HCl. The resulting mixture was extracted with 0.5 L of hexane and the extract was dried over Na$_2$SO$_4$. Filtration and concentration provided the crude title compound which was used for next step without further purification.

Step 5: 8,9-dihydropyrido[1,2-a]indol-7(6H)-one

A solution of the crude product of Step 4 in 1.2 L of toluene was treated with 100 g of silica gel and the mixture was heated to reflux for 6 h. After cooling, the mixture was filtered and the filtrate was concentrated to give the title compound as a dark solid. $^1$H NMR (500 MHz, acetone-d6) δ 7.52 (d, 1H), 7.35 (d, 1H), 7.11 (t, 1H), 7.05 (t, 1H), 6.32 (s, 1H), 4.74 (s, 2H), 3.29 (m, 2H), 2.78 (m, 2H).

Step 6: (+/−)
6,7,8,9-tetrahydropyrido[1,2-a]indol-7-ol

To a cooled (0° C.) solution of the product of Step 5 (12 g) in 150 mL of MeOH was added 2 g of NaBH$_4$. After stirring for 30 min at 0° C., 100 mL of saturated aqueous solution of NH$_4$Cl was added and the mixture was extracted with EtOAc (500 mL). The extract was dried over Na$_2$SO$_4$ and filtered. The filtrate was concentrated to give the crude title compound which was used for next step without further purification. $^1$H NMR (500 MHz, acetone-d6) δ 7.46 (d, 1H), 7.30 (d, 1H), 7.07 (t, 1H), 7.00 (t, 1H), 6.15 (s, 1H), 4.40 (m, 1H), 4.25 (dd, 1H), 3.91 (dd, 1H), 3.20 (m, 1H), 2.46 (m, 1H), 2.10 (m, 1H). 2.00 (m, 1H).

Step 7: (+/−)
7-azido-6,7,8,9-tetrahydropyrido[1,2-a]indole

To a solution of the crude product (~12 g) of Step 6 in CH$_2$Cl$_2$ (150 mL) THF cooled at −40° C. was added 14 mL of Et$_3$N and 5 mL of MeSO$_2$Cl. The reaction mixture was stirred at −40° C. and then quenched by addition of 200 mL of saturated aqueous Na$_2$CO$_3$ solution. The mixture was extracted with 500 mL of EtOAc and the extract was dried over Na$_2$SO$_4$. After filtration, the filtrate was concentrated to give the crude mesylate, which was dissolved in 150 mL of DMF and treated with 10 g of NaN$_3$. The reaction mixture was stirred at 65° C. for 24 h and then concentrated under vacuum. The residue was portioned between 200 mL brine and 500 mL of 1:1 EtOAc/hexane. The organic layer was separated and dried over Na$_2$SO$_4$. After filtration, the filtrate was concentrated to give the crude title compound as a syrup, which was used for next step without further purification. $^1$H NMR (500 MHz, acetone-d6) δ 7.48 (d, 1H), 7.35 (d, 1H), 7.10 (t, 1H), 7.03 (t, 1H), 6.20 (s, 1H), 4.47 (m, 1H), 4.35 (dd, 1H), 4.06 (dd, 1H), 3.15 (m, 1H), 3.05 (m, 1H), 2.25 (1H), 2.10 (m, 1H).

Step 8: (+/−) 4-fluoro-N-(6,7,8,9-tetrahydropyrido[1,2-a]indol-7-yl)benzenesulfonamide A solution of the product from Step 7 (~12 g) and Pd/C (10%, 2 g) in 300 mL MeOH was stirred under a balloon pressure of hydrogen for 24 h. The reaction mixture was then filtered through celite and the filtrate was concentrated to give the amine intermediate. The crude amine (~8 g) was dissolved in 200 mL of CH$_2$Cl$_2$ and treated with 10 mL of Et$_3$N and 5 g of 4-fluorobenzenesulfonyl chloride. The reaction mixture was stirred for 6 h at room temperature and 200 mL of saturated aqueous solution of NaHCO$_3$ was added. The mixture was extracted 400 mL of CH$_2$Cl$_2$ and the extract was over Na$_2$SO$_4$. Filtration, concentration and swishing from 2:1 hexane/EtOAc provided the title compound (6 g). $^1$H NMR (500 MHz, acetone-d6) δ 8.08 (m, 2H), 7.55 (m, 1H), 7.52 (t, 2H), 7.20 (m, 2H), 7.08 (t, 1H), 7.01 (t, 1H), 6.15 (s, 1H), 4.23 (dd, 1H), 3.98 (m, 1H), 3.85 (dd, 1H), 3.10 (m, 1H), 2.93 (m, 1H), 1.90-2.10 (m, 2H).

Step 9: (+/−) 4-fluoro-N-methyl-N-(6,7,8,9-tetrahydropyrido[1,2-a]indol-7-yl)benzenesulfonamide To a solution of the product from Step 8 (3 g) in 100 mL of DMF were added 0.4 g of NaH (60% in mineral oil) and 1.2 mL of MeI. After stirring for 1 h at room temperature, 1 mL of AcOH was added and the mixture was concentrated under vacuum and the residue was dissolved in 200 mL of 1:1 hexane/EtOAc and filtered through a pad of silica gel. The filtrate was concentrated and the residue was swished from 2:1 hexane/EtOAc to give 2.5 g of the title product. $^1$H NMR (500 MHz, acetone-d$_6$) δ 8.10 (m, 2H), 7.47 (m, 3H), 7.28 (d, 1H), 7.09 (dd, 1H), 7.02 (dd, 1H), 6.15 (s, 1H), 4.55 (m, 1H), 4.20 (m, 1H), 3.88 (t, 1H), 3.05-3.12 (m, 1H), 2.92-3.02 (m, 1H), 2.97 (s, 3H), 1.92-2.02 (m, 1H), 1.66 (m, 1H).

Step 10: (+/−) methyl {7-[[(4-fluorophenyl)sulfonyl](methyl)amino]-6,7,8,9-tetrahydropyrido[1,2-a]indol-10-yl}(oxo)acetate To a solution of 0.9 g of the product of Step 9 in 50 mL of CH$_2$Cl$_2$ was added 0.42 mL of oxalyl chloride at 0° C. After stirring for 1 h at 0° C., 4 mL of MeOH was added and the mixture was stirred for another hour and quenched with 30 mL of saturated aqueous solution of NaHCO$_3$. The mixture was extract with 50 mL of CH$_2$Cl$_2$ and the extract was dried over Na$_2$SO$_4$. After filtration, the filtrated was concentrated to give 1.2 of the title product as a solid. $^1$H NMR (500 MHz, acetone-d6) d 8.11 (m, 2H), 7.92 (m, 1H), 7.45-7.52 (m, 3H), 7.28-7.34 (m, 2H, 4.70 (m, 1H), 7.32 (m, 1H), 4.12 (t, 1H), 3.97 (s, 3H), 3.48-3.55 (m, 1H), 3.08-3.07 (m, 1H), 3.00 (s, 3H), 2.10 (m, 1H), 1.76 (m, 1H).

Step 11: (+/−) methyl {7-[[(4-fluorophenyl)sulfonyl](methyl)amino]-6,7,8,9-tetrahydropyrido[1,2-a]indol-10-yl}acetate To a solution of 0.8 g of the product of Step 10 in 100 mL of MeOH and 20 mL of THF was added 0.3 g of NaBH$_4$. After stirring for 1 h at room temperature, 2 mL of AcOH was added and the reaction mixture was concentrated and the residue was portioned between 50 mL of brine and 150 mL of EtOAc. The organic layer was separated and dried over Na$_2$SO$_4$. After filtration, the filtrate was concentrated and the residue was dissolved in 5 mL of CH$_2$Cl$_2$, and treated with 5 mL of Et$_3$SiH and 3 mL of TFA. After stirring for 30 min at room temperature, the reaction mixture was concentrated and the residue was purified by Combiflash eluted with a gradient up to 70% EtOAc/hexane to give 0.3 g of the title compound. $^1$H NMR (500 MHz, acetone-d6) δ 8.10 (m, 2H), 7.45-7.52 (m, 3H), 7.27 (d, 1H), 7.10 (m, 1H), 7.01 (m, 1H), 4.53 (m, 1H), 4.18 (m, 1H), 3.88 (t, 1H), 3.60 (s, 3H), 3.13 (m, 1H), 2.97 (s, 3H), 2.86 (m, 1H), 1.90-2.00 (m, 1H), 1.70 (m, 1H).

Step 12: (+/−) {7-[[(4-fluorophenyl)sulfonyl](methyl)amino]-6,7,8,9-tetrahydropyrido[1,2-a]indol-10-yl}acetic acid To a solution of the product of Step 11 (0.38 g) in 10 mL of THF were added 5 mL of MeOH and 5 mL of 1N LiOH. After stirring for 2 h, 2 mL of AcOH was added and the mixture was partitioned between 50 mL of EtOAc and 20 mL of brine. The EtOAc extract was dried over Na2SO4 and filtered. The filtrate was concentrated and the residue was swished from 3:1 EtOAc/hexane to give 0.18 g of the title compound. $^1$H NMR (500 MHz, acetone-d6) δ 8.11 (m, 2H), 7.53 (d, 1H), 7.47 (t, 2H), 7.28 (d, 1H), 7.10 (dd, 1H), 7.04 (dd, 1H), 4.53 (m, 1H), 4.20 (m, 1H), 3.90 (t, 1H), 3.67 (d, 1H, A of AB), 3.60 (d, 1H, B of AB), 3.15 (m, 1H), 2.97 (3H), 2.85-2.92 (m, 1H), 1.90-2.00 (m, 1H), 1.70 (m, 1H).

Example 2

(+/−) (2E)-3-{7-[[(4-Fluorophenyl)sulfonyl](methyl)amino]-6,7,8,9-tetrahydropyrido[1,2-a]indol-10-yl}acrylic acid

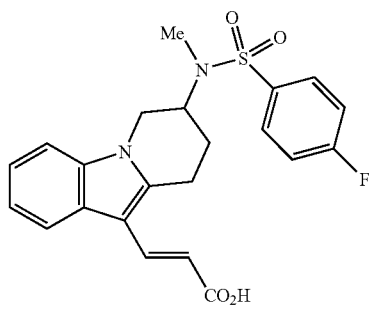

Step 1: (+/−) 4-fluoro-N-(10-formyl-6,7,8,9-tetrahydropyrido[1,2-a]indol-7-yl)-N-methylbenzenesulfonamide To a solution of the product from Step 9 of Example 1 (15 mg) in 2 mL of DMF was added 15 µL of $POCl_3$. After stirring for 10 min, 2 mL of water was added and the reaction mixture was stirred for 24 h. The solid was collected by filtration to give the title compound (~16 mg). $^1$H NMR (500 MHz, acetone-d6) δ 10.11 (s, 1H), 8.15 (m, 1H), 8.10 (m, 2H), 7.48 (t, 2H), 7.45 (m, 1H), 7.27 (m, 2H), 4.68 (m, 1H), 4.30 (m, 1H), 4.06 (t, 1H), 3.62-3.68 (m, 1H), 3.18-3.27 (m, 1H), 3.10 (s, 3H), 2.10 (m, 1H), 1.78 (m, 1H).

Step 2: (+/−) ethyl (2E)-3-{7-[[(4-fluorophenyl)sulfonyl](methyl)amino]-6,7,8,9-tetrahydropyrido[1,2-a]indol-10-yl}acrylate To a solution of triethyl phosphonoacetate (1.12 g) in 20 mL of DMF was added 0.2 g of NaH (60% in mineral oil). After stirring for 0.5 h, 0.2 g of the product from Step 1 was added and the reaction mixture was stirred for 18 h. AcOH (1 mL) was added and the mixture was concentrated under vacuum. The residue was suspended in 20 mL of EtOAc and filtered through a pad of silica gel. The filtrate was concentrated and the residue was swished from 2:1 EtOAc to give 0.22 g of the title compound. $^1$H NMR (500 MHz, acetone-d6) δ 8.10 (m, 2H), 7.98 (d, 1H), 7.98 (m, 1H), 7.47 (t, 2H), 7.42 (m, 1H), 7.25 (m, 2H), 6.28 (d, 1H), 4.62 (m, 1H), 4.27 (m, 1H), 4.21 (q, 2H), 4.02 (t, 1H), 3.48 (1H), 3.07 (m, 1H), 3.00 (3H), 2.08 m, 1H), 1.77 (m, 1H), 1.27 (t, 3H).

Step 3: (+/−) (2E)-3-{7-[[(4-fluorophenyl)sulfonyl](methyl)amino]-6,7,8,9-tetrahydropyrido[1,2-a]indol-10-yl}acrylic acid A solution of 85 mg of the product from Step 2 in 2 mL of THF and 3 mL of MeOH was added 0.5 mL of 2N NaOH. The mixture was heated at 50° C. for 8 h and 1 mL of AcOH was then added, and concentrated. The residue was suspended in 5 mL of water and the solid was collected by filtration, and then purified by Combiflash eluted with a gradient up to 70% EtOAc/hexane containing 5% of AcOH to give 9 mg of the title compound (eluted first). $^1$H NMR (500 MHz, acetone-d6) d 8.12 (m, 2H), 7.87 (d, 1H), 7.87 (m, 1H), 7.48 (t, 1H), 7.42 (m, 1H), 7.28 (m, 2H), 6.28 (d, 1H), 4.65 (m, 1H), 4.27 (m, 1H), 4.04 (t, 1H), 3.49 (m, 1H), 3.10 (m, 1H), 3.02 (s, 3H), 2.10 (m, 1H), 1.78 (m, 1H).

Example 3

(+/−) (2E)-3-{7-[[(4-Methoxyphenyl)sulfonyl](methyl)amino]-6,7,8,9-tetrahydropyrido[1,2-a]indol-10-yl}acrylic acid

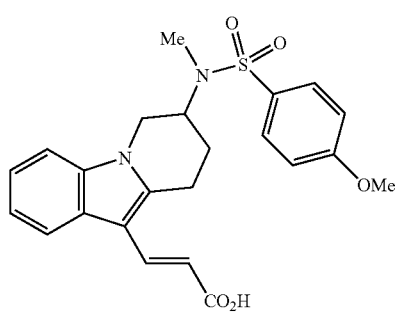

The slower eluting fraction from Combiflash in Step 3 of Example 2 provided 20 mg of the title compound. $^1$H NMR (500 MHz, acetone-d6) d 7.94 (d, 2H), 7.48 (d, 1H), 7.48 (m, 1H), 7.41 (m, 1H), 7.25 (m, 2H), 7.20 (d, 2H), 6.28 (d, 1H), 4.58 (m, 1H), 4.23 (m, 1H), 4.00 (t, 1H), 3.96 (s, 3H), 3.36 (m, 1H), 3.05 (m, 1H), 2.95 (s, 3H), 2.02 (m, 1H), 1.23 (m, 1H).

Biological Assays

Radioligand binding assay. Radioligand binding assays were performed at room temperature in 10 mM HEPES/KOH pH 7.4, 1 mM EDTA containing 10 mM $MnCl_2$ and 0.4 nM [$^3$H]$PGD_2$ (NEN, 172 Ci mmol$^{-1}$), in a final volume of 0.2 ml. Competing ligands were diluted in dimethylsulfoxide ($Me_2SO$) that was kept constant at 1% (v/v) of the final incubation volume. The reaction was initiated by the addition of 23 µg of membrane protein prepared from a HEK-hCRTH2 cell line. Total and non-specific binding were determined in the absence and the presence of 10 µM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted Unifilters GF/C (Packard), using a Tomtec MachIII semi-automated harvester (for HEK-hCRTH2). The filters were then washed with 4 ml of the same buffer and residual radioligand bound to the filter was determined by liquid scintillation counting following equilibration in 5 ml Ultima Gold™ (GF/C) or 50 µl Ultima Gold F™ (Unifilter) (Packard).

i[cAMP] measurements. HEK-hCRTH2 cells were grown to confluency on the day of the assay. The cells were washed with PBS, incubated for 3 min in cell dissociation buffer, harvested by centrifugation at 300 g for 6 min at room temperature and resuspended at 10$^6$ cells ml$^{-1}$ in Hanks' balanced salt solution containing 25 mM HEPES pH 7.4 (HBSS/HEPES). The assay was performed in 0.2 ml HBSS/HEPES containing 100 000 cells, 5 µM forskolin (Sigma), 100 µM RO 20-1724 (Biomol) and the test compound at various concentrations. Following a 10 min pre-incubation of the cells with the test compound at 37° C., $PGD_2$ was added at a concentration of 3 µM to initiate the reaction. Following a 10 min incubation at 37° C., the reaction was stopped by a 3 min incubation in a boiling water bath. The samples were centrifuged for 10 min at 500 g and the cAMP content in the supernatant was determined using a [$^{125}$I]-cAMP scintillation proximity assay (Amersham). Maximal inhibition of forskolin stimulated cAMP production by activation of CRTH2 was determined in the presence of 1 μM PGD$_2$. All compounds were prepared in Me$_2$SO kept constant at 1% (v/v) of the final incubation volume.

What is claimed is:

1. A compound of the formula I:

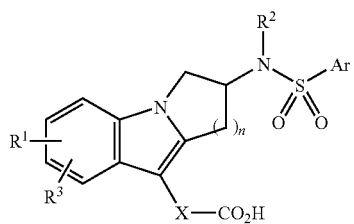

and pharmaceutically acceptable salts thereof, wherein:
n is 1 or 2;
Ar is aryl or heteroaryl each optionally substituted with 1 to 4 groups independently selected from R$^c$;
X is selected from —C(R$^a$)(R$^b$)—, —C(R$^a$)(R$^b$)—C(R$^a$)(R$^b$)—, —C(R$^a$)=C(R$^a$)—, —OC(R$^a$)(R$^b$)—, and —SC(R$^a$)(R$^b$)—;
R$^1$ is selected from H, halogen and C$_{1-6}$alkyl;
R$^2$ is selected from H and C$_{1-6}$alkyl;
R$^3$ is selected from H, halogen, C$_{1-6}$alkyl, OC$_{1-6}$alkyl, SC$_{1-6}$alkyl, S(O)$_n$C$_{1-6}$alkyl, CN, aryl and heteroaryl;
R$^a$ and R$^b$ are independently H, halogen, aryl, heteroaryl, C$_{1-6}$alkyl or haloC$_{1-6}$alkyl; or
R$^a$ and R$^b$ together with the carbon atom to which they are both attached complete a C$_{3-6}$cycloalkyl ring; or
R$^a$ and R$^b$ together with the adjacent carbon atoms to which they are attached complete a C$_{3-6}$cycloalkyl ring; and
R$^c$ is selected from halogen, CN, C$_{1-6}$alkoxy, C$_{1-6}$alkyl, haloC$_{1-6}$alkoxy, and haloC$_{1-6}$alkyl.

2. A compound of claim 1 wherein n is 1.
3. A compound of claim 1 wherein n is 2.
4. A compound of claim 1 wherein Ar is phenyl optionally substituted with 1 to 3 groups independently selected from R$^c$.
5. A compound of claim 1 wherein Ar is phenyl substituted with 1 to 2 groups independently selected from halogen and C$_{1-6}$alkoxy.
6. A compound of claim 1 wherein X is —C(R$^a$)(R$^b$)—.
7. A compound of claim 1 wherein X is methylene.
8. A compound of claim 1 wherein X is —C(R$^a$)(R$^b$)—C(R$^a$)(R$^b$)— or —C(R$^a$)=C(R$^a$)—.
9. A pharmaceutical composition comprising a therapeutically effective amount of a compound of claim 1 and a pharmaceutically acceptable carrier.
10. The compound {7-[[(4-fluorophenyl)sulfonyl](methyl)amino]-6,7,8,9-tetrahydropyrido[1,2-a]indol-10-yl}acetic acid or a pharmaceutically acceptable salt thereof.

* * * * *